| United States Patent [19] | [11] Patent Number: 4,689,173 |
| Eckler | [45] Date of Patent: Aug. 25, 1987 |

[54] PENTAERYTHRITOL SLURRIES

[75] Inventor: Paul E. Eckler, Terre Haute, Ind.

[73] Assignee: International Minerals & Chemical Corporation, Terre Haute, Ind.

[21] Appl. No.: 872,571

[22] Filed: Jun. 10, 1986

Related U.S. Application Data

[63] Continuation of Ser. No. 708,451, Mar. 5, 1985, abandoned.

[51] Int. Cl.$^4$ ............................................. B01J 13/00
[52] U.S. Cl. ....................................... 252/308; 406/47; 406/197
[58] Field of Search ................. 252/308; 406/47, 197; 568/853

[56] References Cited

U.S. PATENT DOCUMENTS 2,251,236  7/1941  Wyler et al. .................... 568/853 X
3,082,257  3/1963  Karabinos et al. ............. 252/351 X

FOREIGN PATENT DOCUMENTS 459840  9/1949  Canada ............................... 252/308

OTHER PUBLICATIONS

Burrell et al.: "Polypentaerythritol Varnishes", reprinted from Paint, Oil & Chemical Review, issue of Dec. 14, 1944.
Berlow et al.: *The Penterythritols*, Reinhold Publ. Corp., New York, 1958, pp. 25-29.

*Primary Examiner*—Richard D. Lovering
*Attorney, Agent, or Firm*—Robert H. Dewey; Thomas L. Farquer

[57] ABSTRACT

Slurries of pentaerythritol in a liquid oil in which pentaerythritol is substantially insoluble are disclosed. The slurries can contain up to 70 percent by weight or more of solid pentaerythritol. Suitable oils include propylene glycol, ethylene glycol, vegetable oils, glycerin and tall oil fatty acid. The slurries are stable and flowable allowing for shipment in bulk.

16 Claims, No Drawings

PENTAERYTHRITOL SLURRIES

This application is a continuation, of application Ser. No. 708,451, filed Mar. 5, 1985, now abandoned.

BACKGROUND OF THE INVENTION

The present invention relates to stable and flowable pentaerythritol slurries which are suitable for shipment in bulk.

Pentaerythritol (PE) is a five carbon polyol useful as a starting material in the paint, varnish and synthetic resins industries. PE is a solid at room temperature resulting in its commercial availability as a solid. There are many disadvantages associated with the handling and transportation of solids, such as, for example, high handling and packaging costs associated with bagged products, disposal of packaging materials by the end-user and the potential for inhalation of dust by handlers of solids.

It is apparent that there is a need for a liquid grade of PE that is stable and flowable which would allow for shipment of the liquid grade PE in bulk quantities.

SUMMARY OF THE INVENTION

Briefly, in accordance with the present invention, a stable flowable pentaerythritol (PE) slurry is prepared by mixing PE with an oil in which PE is substantially insoluble. The oil serves as the liquid phase of the slurry. This PE slurry is suitable for shipment in bulk.

Of particular interest in the practice of the present invention is a PE slurry wherein the liquid phase is ethylene glycol, propylene glycol, glycerin or tall oil fatty acid. The PE can be granular or powdered PE and the solids content, by weight, can vary from 40 to 70 percent.

DETAILED DESCRIPTION OF THE INVENTION

In the practice of the present invention it is essential to employ PE as the solid phase and, as the liquid phase, an oil in which PE is substantially insoluble. The present PE slurries are prepared by mixing the PE and oil in accordance with standard mixing techniques well known to one skilled in the art.

Any solid PE is suitable for practicing the present invention. Technical grade, granular and powdered, PE is preferred. Granular PE having a particle size in the range of from about 0.1 millimeter (mm) to about 1 mm is advantageously employed, while it is preferred to employ granular PE having a particle size in the range of from about 0.2 mm to about 0.5 mm. Powdered PE is finely powdered material of which 90 percent passes through a 325 mesh screen, i.e., 90% of the PE particles have a diameter <0.045 mm. The viscosity of the PE slurries is dependent on the particular oil and the particle size of the PE with finer particle sizes of PE resulting in higher viscosity slurries at a given solids level when compared to larger particle sizes of PE. Powdered PE results in smooth, paint-like slurries at concentrations which result in flowable liquids, i.e. <60% in ethylene glycol and propylene glycol.

Commercially available PE typically contains from about 70 to about 85 percent or more monopentaerythritol and up to about 15 percent of dipentaerythritol. The present invention encompasses the use of PE material containing minor amounts of dipentaerythritol. In one aspect of the present invention, dipentaerythritol can be substituted for the monopentaerythritol thereby providing a dipentaerythritol slurry.

Any oil in which PE is substantially insoluble is acceptable as the liquid phase for the present PE slurries. Suitable oils include ethylene glycol, diethylene glycol, propylene glycol, glycerin, vegetable oils and tall oil fatty acid. Conveniently, the oil in a given slurry will be chosen on the basis of being compatible with the end user's product and the processes involved in preparing that product. Preferred oils include ethylene glycol, propylene glycol and tall oil fatty acid.

The PE slurries of the present invention are prepared by adding the solid PE to the liquid phase oil with agitation. Typically, the solid PE is added to the oil in a high shear mixer, such as the mixers normally used in the preparation of paints, i.e., PREMIER high speed dispersion mill. The solid PE is added in an amount which represents at least about 40 percent by total weight of the slurry composition. Advantageously, the PE is present in the slurry in an amount ranging from about 50 to about 70 percent by weight.

When granular PE is employed as the solid phase of the slurry it is usually desired to employ a solids content of the granular PE of from about 50 to about 70% by weight. When propylene glycol is the oil phase then solids content of from 57% to about 60% will give a slurry having a viscosity similar to glycerin (9.54 poise at 25° C.).

When powdered PE, i.e., 90% passes a 325 mesh, is employed as the solid phase of the slurry it is usually desired to employ a solids content of the powdered PE of from about 40 to about 55% by weight.

In a preferred embodiment of the present invention, granular PE is mixed with ethylene glycol in amounts resulting in the production of a stable, flowable slurry having a solids content of about 69 percent by weight and a viscosity measured at 38.5 poise.

In other embodiments of the present invention, wetting agents or surfactants are optionally added to the oil phase prior to mixing with the solid PE to aid in the dispersability of the PE in the oil. Suitable surfactants include oxazolines, tributyl phosphate, 2-nitropropane, 2-amino-2-methyl-1-propanol, polyoxyethylene ethers and polyethoxylated phenol, such as, TRITON X-100. The surfactants are added to the present slurries in an amount effective to produce desirable surface active properties, usually less than about 5 percent by weight of the slurry. Other additives, such as antimicrobials, can also be added to the present PE slurries.

The following examples illustrate the practice of the present invention but should not be construed as limiting its scope.

EXAMPLE 1

Various slurries of PE were prepared by mixing PE with the liquid phases listed below. The slurries were prepared in a PREMIER high speed dispersion mill using a 2.5 inch diameter COWLES blade in batches of about 400 grams (g). The solid PE was added to the liquid phase with agitation. The properties of the PE slurries are listed below. The viscosities were measured on a BROOKFIELD LVT viscometer using a number 4 spindle (number 3 for 55% technical grade PE) at 30 or 60 rpm (0.6 to 12 rpm for number 3 spindle).

| PE (weight %) | PE Grade | Liquid Phase | Properties | | |
|---|---|---|---|---|---|
| | | | Viscosity (cps) | Density (Lb/gal) | Lb PE/gal |
| 50 | Powder | PG | 2,330 | 9.69 | 4.85 |
| 55 | Powder | PG | 5,810 | 10.07 | 5.54 |
| 55 | Powder | EG | 14,100 | 10.34 | 5.69 |
| 55 | Granular | PG | 666 | 9.82 | 5.40 |
| 70 | Granular | PG | 7,100 | 10.37 | 7.26 |
| 70 | Granular | TOFA | 5,920 | 10.00 | 7.00 |

PG = propylene glycol
EG = ethylene glycol
TOFA = tall oil fatty acid
cps = centipoise
Powdered PE: 90% passes 325 mesh
Granular PE: Bulk retained by a 60 mesh screen and passes through a 40 mesh screen

EXAMPLE 2

Samples of the slurries prepared in Example 1 were placed in small vials and allowed to stand overnight. The 70% granular grade PE slurry in propylene glycol was placed in a one quart jar. In the morning all of the slurries showed no signs of settling with the exception of the 55% granular grade PE slurry which had a clear oily upper layer (17% by volume) and a white opaque lower layer (83% by volume). However, after 4 days the 55% granular grade PE slurry showed no signs of hard settling.

EXAMPLE 3

A PE slurry was prepared employing substantially the same procedures of Example 1 wherein the PE was granular grade PE and the liquid phase was ethylene glycol. The weight ratio of PE/ethylene glycol was 69/31. The viscosity of this slurry was measured to be 38.5 poise by a BROOKFIELD viscometer.

EXAMPLE 4

A PE slurry, similar to the PE slurry described in Example 3, was prepared with the exception that 0.1% (by total weight of the slurry) TRITON X-100 surfactant was added to the ethylene glycol prior to the addition of the PE to it. The surfactant increased the ease of dispersion of the PE into the ethylene glycol. The viscosity of this slurry was measured to be 99.4 poise by a BROOKFIELD viscometer.

EXAMPLE 5

A one quart sample of a slurry containing 70% (by weight) technical grade PE in propylene glycol was prepared employing substantially the same procedures described in Example 1. The slurry was allowed to stand at room temperature for six months. A small (⅛ inch) clear layer formed on the top of the slurry suggesting an insignificant settling of the PE solids. The slurry remained easily mobile and no signs of hard settling were present. Some parts of the slurry developed a slightly gelled consistency. These gel segments were completely broken up upon moderate agitation of the slurry.

In further embodiments, various PE slurries employing various oils and solids content described herein, are prepared which exhibit stable and flowable properties.

I claim:

1. A stable, flowable slurry composition consisting essentially of:
   (a) a solid phase of pentaerythritol or dipentaerythritol or mixture thereof in an amount of from about 40% to about 55% by total weight of the slurry composition when the solid phase is powdered, or from about 50% to about 70% when the solid phase is granular; and
   (b) a liquid phase of an oil in which pentaerythritol or dipentaerythritol or mixture thereof is substantially insoluble, selected from the group consisting of propylene glycol, ethylene glycol, glycerin, and mixtures thereof.

2. The composition of claim 1 comprising propylene glycol and granular pentaerythritol and the pentaerythritol comprises from about 60 to 70 percent by weight of the slurry composition.

3. The composition of claim 1 comprising ethylene glycol and granular pentaerythritol and the pentaerythritol comprises from about 60 to about 70% by weight of the slurry composition.

4. The pentaerythritol slurry composition of claim 3 wherein the pentaerythritol solids content is about 69 percent by weight of the slurry composition.

5. The composition of claim 1 wherein the oil is propylene glycol.

6. The composition of claim 1 wherein the oil is ethylene glycol.

7. The composition of claim 1 wherein the oil is glycerin.

8. The composition of claim 1 wherein the solid phase is granular and comprises from about 60–70% by weight of the slurry composition.

9. The composition of claim 1 wherein the solid phase is pentaerythritol.

10. The composition of claim 1 wherein the solid phase is di-pentaerythritol.

11. The composition of claim 1, wherein the solid phase is powdered and comprises from about 40–55% by weight of the slurry composition.

12. A stable, flowable slurry composition consisting essentially of:
   (a) a solid phase of pentaerythritol or dipentaerythritol or mixture thereof in an amount of from about 40% to about 55% by total weight of the slurry composition when the solid phase is powdered or from about 50% to about 70% when the solid phase is granular and,
   (b) a liquid phase of tall oil fatty acids.

13. The composition of claim 12 wherein the solid phase is granular and is from about 60–70% by weight of the slurry composition.

14. The composition of claim 12 wherein the solid phase is powdered and is from about 40 to about 55% by weight of the slurry composition.

15. The composition of claim 12 wherein the solid phase is pentaerythritol.

16. The composition of claim 12 wherein the solid phase is dipentaerythritol.

* * * * *